United States Patent
Jomaa et al.

(10) Patent No.: US 7,871,992 B2
(45) Date of Patent: *Jan. 18, 2011

(54) ORGANOPHOSPHOROUS COMPOUNDS FOR THE ACTIVATION OF GAMMA/DELTA T CELLS

(75) Inventors: Hassan Jomaa, Giessen (DE); Oliver Wolf, Florstadt (DE); Boran Altincicek, Fernwald-Annerod (DE); Mathias Eberl, Giessen (DE); Martin Hintz, Giessen (DE); Ann-Kristin Kollas, Giessen (DE); Armin Reichenberg, Butzbach (DE); Jochen Wiesner, Giessen (DE)

(73) Assignee: Bioagency AG, Hamburg (DE)

( * ) Notice: Subject to any disclaimer, the term of this patent is extended or adjusted under 35 U.S.C. 154(b) by 295 days.

This patent is subject to a terminal disclaimer.

(21) Appl. No.: 12/137,241

(22) Filed: Jun. 11, 2008

(65) Prior Publication Data

US 2008/0249067 A1 Oct. 9, 2008

Related U.S. Application Data

(63) Continuation of application No. 10/484,143, filed as application No. PCT/EP02/07986 on Jul. 18, 2002, now Pat. No. 7,399,756.

(30) Foreign Application Priority Data

Jul. 20, 2001 (DE) .................. 101 34 705
Jul. 25, 2001 (DE) .................. 101 35 395

(51) Int. Cl.
*A61K 31/66* (2006.01)
(52) U.S. Cl. .................. 514/108; 514/102
(58) Field of Classification Search .......... 514/108, 514/102
See application file for complete search history.

(56) References Cited

U.S. PATENT DOCUMENTS

| 5,639,653 | A | 6/1997 | Bloom et al. |
| 5,902,793 | A | 5/1999 | Bloom et al. |
| 6,534,050 | B1 | 3/2003 | Tanaka et al. |
| 6,624,151 | B1 | 9/2003 | Belmant et al. |
| 6,660,723 | B1 | 12/2003 | Belmant et al. |
| 7,399,756 | B2 * | 7/2008 | Jomaa et al. .................. 514/108 |

FOREIGN PATENT DOCUMENTS

| CA | 2334711 A1 | 12/2000 |
| CA | 2444955 A1 | 10/2003 |
| OA | 11718 | 1/2005 |
| WO | WO 95/20673 A1 | 8/1995 |
| WO | WO 00/00182 A2 | 1/2000 |
| WO | WO 00 30653 A2 | 6/2000 |
| WO | WO 00 59916 A1 | 10/2000 |
| WO | WO 01/22816 A1 | 4/2001 |
| WO | WO 01/94561 A2 | 12/2001 |
| WO | WO 02/12478 A2 | 2/2002 |
| WO | WO 02/083720 A2 | 10/2002 |
| WO | WO 02/095011 A2 | 11/2002 |
| WO | WO 03/038072 A1 | 5/2003 |

OTHER PUBLICATIONS

Belmant, C. et al. "3-Formyl-1-butyl pyrophosphate a novel mycobacterial metabolite-activating human gamma delta T cells" *J. Biol. Chem*, 1999, pp. 32079-32084, vol. 274, No. 45.

Takagi, M. et al. "Studies on the nomevalonate pathway: Formation of 2-C-methyl-Derythritol 2,4-cyclodiphosphate from 2-phospho-4(cytidine 5'-diphospho)-2-C-methyl-Derythritol" Tetrahedron Letters, 2000, pp. 3395-3398, vol. 41.

Tanaka, Y. et al. "Natural and synthetic non-peptide antigens recognized by human gamma delta T cells" *Nature*, May 11, 1995, pp. 155-158, vol. 375, No. 6527.

McClard, R.W. et al. "Novel phosphonylphosphinyl (P-C-P-C-) analogues of biochemically interesting diphosphates. Syntheses and properties of P-C-P-C-, analogues of isopentenyl diphosphate and dimethylallyl diphosphate" *J. Am. Chem. Soc.*, 1987, pp. 5544-5545, vol. 109.

Jacob, L. et al. "On the influence of phosphoric ester groups in geranyldiphosphate biosynthesis" *Bull. Soc. Chim. de France*, 1990, pp. 719-733, vol. 127, No. 6.

Sireci, G. et al. "Differential activation of human gamma delta cells by nonpeptide phosphoantigens" *Eur. J. Immunol.*, 2001, pp. 1628-1635, vol. 31.

Belmant, C. et al. "A chemical basis for selective recognition of nonpeptide antigens by human delta T cells," Faseb *J.*, Sep. 2000, pp. 1669-1670, vol. 14.

Hintz, M. et al. "Identification of (*E*)-4-hydroxy-3-methyl-but-2-enyl pyrophosphate as a major activator for human gamma delta T cells in *Escherichia coli*" *Febs Lett.*, 2001, pp. 317-322, vol. 509.

(Continued)

*Primary Examiner*—Rei-tsang Shiao
(74) *Attorney, Agent, or Firm*—Saliwanchik, Lloyd & Saliwanchik

(57) ABSTRACT

The present invention describes organophosphorus compounds of general formula (I)

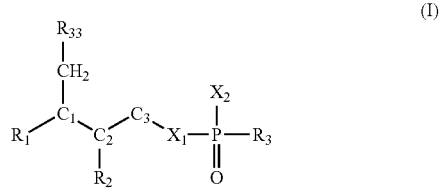

their preparation and their uses in the activation of gamma/delta T-cells, in the screening of GcpE and LytB enzyme inhibitors and in the prophylaxis and treatment of diseases in humans and animals.

16 Claims, No Drawings

OTHER PUBLICATIONS

Feurle, J. et al. "*Echericheria coli* produces phosphoantigens activating human gamma delta T cells" *J. Biol. Chem.*, Jan. 4, 2002, pp. 148-154, vol. 277, No. 1.

Espinosa, E. "Synaptic transfer by human gamma delta T cells stimulated with soluble or cellular antigens" *J. Immunol.*, 2002, pp. 6336-6343, vol. 168.

Gao, W. et al. "(*E*)-4-hydroxy-3-methylbut-2-enyl diphosphate: An intermediate in the formation of terpenoids in plant Chromoplasts" *Angew. Chem Int Ed.*, 2002, pp. 2604-2607, vol. 41, No. 14.

Fox, D.T. et al. "Synthesis of (*E*)-4-hydroxydimethylallyl diphosphate. An intermediate in the methyl erythritol phosphate branch of the isoprenoid pathway" *J. Org. Chem.*, 2002, pp. 5009-5010, vol. 67, No. 14.

O'Brien, R.S. et al. "Depletion of a γσ T cell subset can increase host resistance to a bacterial infection" *J. Immunol.*, 2000, pp. 6472-6479, vol. 165.

Schwender, J. "Die mevalonat-unabhängige isoprenoid-biosynthese und deren verbreitung in pflanzen" *Dissertation, Universität Karlsruhe (Th)* Nov. 10, 1999, pp. I-X and 1-168.

Santini, D. et al. "The antineoplastic role of bisphosphonates: from basic research to clinical evidence" *Ann. Oncol.*, 2003, pp. 1468-1476, vol. 14.

Espinosa, E. et al. "Chemical synthesis and biological activity of bromohydrin pyrophosphate, a potent stimulator of human γσ T cells" *J. Biol. Chem.*, May 25, 2001, pp. 18337-18344, vol. 276, No. 21.

Brondino, C. et al. "Synthesis of new phosphonic derivatives with fluorinated chains" *J. Fluorine Chem.*, 1996, pp. 193-200, vol. 76.

Kunzmann, V. et al. "Stimulation of γσ T cells by aminobisphosphonates and induction of antiplasma cell activity in multiple myeloma" *Blood*, Jul. 15, 2000, pp. 384-392, vol. 96, No. 2.

Valentijn, A.R.P.M. et al. "An expeditious synthesis of pyrophosphate analogues of farnesyl pyrophosphate using the phosphonylating agent methyl methylphosphonomorpholidate" *Synlett*, Sep. 1991, pp. 663-664.

Beytia, E.D. et al. "Biochemistry of polyisoprenoid biosynthesis" *Annu. Rev. Biochem.*, 1976, pp. 113-142, vol. 45.

Rohmer, M. "The discovery of a mevalonate-independent pathway for isoprenoid biosynthesis in bacteria, algae and higher plants" *Nat. Prod. Rep.*, 1999, pp. 565-574, vol. 16.

Jomaa, H. et al. "Vγ9/Vσ2 T cell activation induced by bacterial low molecular mass compounds depends on the 1-deoxy-D-xylulose 5-phosphate pathway of isoprenoid biosynthesis" *FEMS Immunol. and Med. Microbiol.*, 1999, pp. 371-378, vol. 25.

Ward, J.L. et al. "Synthesis of (2*E*)-4-hydroxy-3-methylbut-2-enyl diphosphate, a key intermediate in the biosynthesis of isoprenoids" *J. Chem. Soc., Perkin Trans.* 1, 2002, pp. 710-712.

Seemann, M. et al. "Isoprenoid biosynthesis in *Escherichia coli* via the methylerythritol phosphate pathway: enzymatic conversion of methylerythritol cyclodiphosphate into a phosphorylated derivative of (*E*)-2-methylbut-2-en3-1,4-diol" *Tetrahedron Lett.*, 2002, pp. 1413-1415, vol. 43.

Woodside, A.B. et al. "Trisammonium geranyl diphosphate" *Org. Synth.*, 1988, pp. 211-219, vol. 66.

Sato, K. et al. "A new synthesis of α-santalol" *Bull. Chem. Soc. Jpn.*, 1976, pp. 3351-3352, vol. 49, No. 11.

Hiroi, K. et al. "Palladium-catalyzed intramolecular metallo-ene reactions using allylic sulfones as enophiles" *Chem. Pharm. Bull.*, 1994, pp. 786-791, vol. 42, No. 4.

Lensky, S. et al. "Use of Cyclic Phosphonic Acid Esters for Treatment of Brain Function Disorders and Depression", *CAS*, 1999, 130:191901.

Brown, R.J. et al. "Isopentenyl pyrophosphate isomerase and/or prenyl transferaase inhibitors for therapeutic use", *CAS*, 1997, 128:30414.

Belmant, C. et al. "Monoesters of methylenediphosphonic acids and salts selectively inhibiting Tγ9δ2 lymphocytes", *CAS*, 2000, 133:276336.

Sciammas, R. et al. "TCRγσ cells and viruses" *Microbes and Infection*, 1999, pp. 203-212.

Espinosa, E. et al. "Y2K+1 state-of-the-art on non-peptide phosphoantigens, a novel category of immunostimulatory molecules" *Microbes and Infection*, 2001, pp. 645-654.

Fournie, J. J. et al. "Stimulation of γσT cells by phosphoantigens" *66th Forum in Immunology*, May 9, 1996, pp. 338-347.

\* cited by examiner

ORGANOPHOSPHOROUS COMPOUNDS FOR THE ACTIVATION OF GAMMA/DELTA T CELLS

CROSS REFERENCE TO RELATED APPLICATIONS

This application is a continuation of U.S. application Ser. No. 10/484,143, filed on Oct. 22, 2004, which is the national stage of international application No. PCT/EP02/07986, filed Jul. 18, 2002, which are incorporated herein by reference in their entireties, including all references, Figures, Tables and nucleic acid and polynucleotide sequences.

Numerous diseases in humans and animals are caused by the abnormal functioning of the immune system. Consequently, there is a high demand for substances that are able to regulate the immune system.

It is known how to employ the classical acetate/mevalonate pathway in the biosynthesis of isoprenoids (Beycia E D, Porter J W, Annu Rev Biochem. 1976; 45:113-42), and an alternative method of biosynthesis is known that is independent of mevalonate, namely the 2-methyl-D-erythritol pathway (MEP, synonymous with DOXP) (Rohmer M. Nat Prod Rep. 1999 October; 16(5):565-74). Both pathways lead to isopentenyl pyrophosphate (IPP), the common precursor of all higher isoprenoids. While the acetate/mevalonate pathway has been known for a long time and has been thoroughly explained, not all biosynthetic reaction steps that occur along the MEP are as yet known.

It is known that human gamma/delta T-cells are activated by one or several intermediates along the MEP. This means that a selective proliferation and cytokine secretion of the gamma/delta T-cell population is brought about during the incubation of peripheral blood lymphocytes with extracts from organisms that possess the MEP (Jomaa H, Feurle J, Luhs K, Kunzmann V, Tony H P, Herderich M, Wilhelm M, FEMS Immunol Med Microbiol, 1999 September; 25(4): 371-8). The exact chemical composition of this/these activating substance(s) is still unknown. The published data indicate that 3-formyl-1-butyl pyrophosphate is formed as a hypothetical intermediate of the MEP and that it plays a role in the activation of gamma/delta T-cells (Belmant C, Espinosa E, Poupot R, Peyrat M A, Guiraud M, Poquet Y, Bonneville M, Fournie J J, J Biol., Chem. 1999 Nov. 5; 274(45):32079-84).

The object of this invention is to provide substances which are able to stimulate gamma/delta T-cells and thereby have a regulatory effect on the immune system.

This object is achieved by medicines which contain one or more of the substances defined in claim 1 as well as in the subordinate claims.

Surprisingly, it has been found that compounds of formula (I) are eminently suitable for the activation of gamma/delta T-cells.

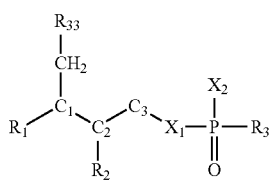
(I)

wherein $R_1$ is selected from the group comprising a methyl residue, a formyl residue, substituted and unsubstituted hydroxymethyl residues and $C_0H_2R_{31}$, wherein $R_{31}$ is selected from the group comprising OH, substituted and unsubstituted phosphate and substituted and unsubstituted pyrophosphate and $R_{31}$ and $R_2$ cannot be present in the molecule at the same time, $R_{33}$ is selected from the group comprising hydrogen, OH, substituted and unsubstituted phosphate and substituted and unsubstituted pyrophosphate, $R_3$ is selected from the group comprising hydrogen, substituted and unsubstituted alkyl with 1 to 26 carbon atoms, substituted and unsubstituted hydroxyalkyl with 1 to 26 carbon atoms, substituted and unsubstituted aryl, substituted and unsubstituted aralkyl, substituted and unsubstituted alkenyl with 1 to 26 carbon atoms, substituted and unsubstituted alkinyl with 1 to 26 carbon atoms, substituted and unsubstituted cycloalkyl, substituted and unsubstituted heterocyclic residues, substituted and unsubstituted phosphate, a silyl, a nucleoside, a nucleoside mono-, di- or triphosphate, a deoxynucleoside, a cation of an organic or inorganic base, particularly a metal of the first, second or third main group of the Periodic Table, ammonium, substituted ammonium and ammonium compounds derived from ethylenediamine or amino acids, and $OR_{34}$, wherein $R_{34}$ is defined like $R_3$, $X_2$, inasmuch as a ring is formed between $X_2$ and $C_1$, is defined like $X_1$, and otherwise $X_2$ is selected from the group comprising —$OR_6$,

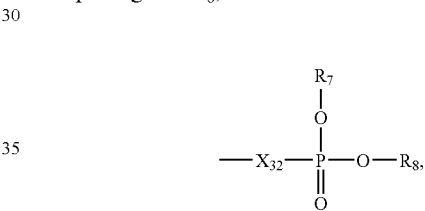

wherein $R_7$ and $R_8$ are defined like $R_{34}$,

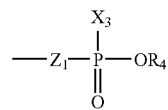

wherein $R_4$ is defined like $R_3$, and $Z_7$ is defined like $X_1$, and $X_3$, if it forms a ring with $C_1$, is defined like $X_1$ and, if does not form a ring with $C_1$, corresponds to a group

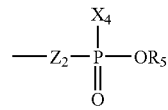

wherein $R_5$ is defined like $R_3$, and $Z_2$ and $X_4$, which forms a ring with $C_1$, are defined like $X_1$, $R_2$ is selected from the group comprising hydrogen, OH, alkoxy, phenoxy, benzyloxy, substituted and unsubstituted phosphate and substituted and unsubstituted pyrophosphate, $X_1$ can be oxygen or

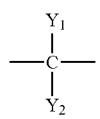

wherein $Y_1$ and $Y_2$ can be the same or can be different and are selected from the group comprising H, OH, halogen, an amino residue, a $C_{1-9}$-alkoxy residue and a $C_{1-9}$-alkylthio residue, or together form an oxo group, and a double bond can be present between $C_0$ and $C_1$, or between $C_1$ and $C_2$, or between $C_2$ and $C_3$.

Preference is given to compounds having the formula:

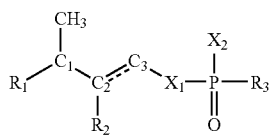
(II)

wherein a single or double bond is present between $C_2$ and $C_3$, $R_1$ is selected from the group comprising a methyl residue, a formyl residue and substituted and unsubstituted hydroxymethyl residues, $R_2$ is selected from the group comprising hydrogen, hydroxyl, alkoxy, phenoxy and benzyloxy residues, substituted and unsubstituted phosphate and substituted and unsubstituted pyrophosphate, $X_1$ is oxygen or corresponds to a group

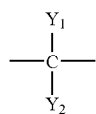

wherein $Y_1$ and $Y_2$ can be the same or can be different and are selected from the group comprising H, OH, halogen, amino and $C_{1-9}$-alkoxy and $C_{1-9}$-alkylthio residues, or together form an oxo group, $R_3$ is selected from the group comprising hydrogen, substituted and unsubstituted alkyl with 1 to 26 carbon atoms, substituted and unsubstituted hydroxyalkyl with 1 to 26 carbon atoms, substituted and unsubstituted aryl, substituted and unsubstituted aralkyl, substituted and unsubstituted alkenyl with 1 to 26 carbon atoms, substituted and unsubstituted alkinyl with 1 to 26 carbon atoms, substituted and unsubstituted cycloalkyl, substituted and unsubstituted heterocyclic residues, substituted and unsubstituted phosphate, a silyl, a nucleoside, a nucleoside mono-, di- or triphosphate, a deoxynucleoside, a cation of an organic or inorganic base, particularly a metal of the first, second or third main group of the Periodic Table, ammonium, substituted ammonium and ammonium compounds derived from ethylenediamine or amino acids, $X_2$, inasmuch as a ring is formed between $X_2$ and $C_1$, is defined like $X_1$, and otherwise $X_2$ corresponds to

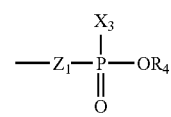

wherein $R_4$ is defined like $R_3$, and $Z_1$ is defined like $X_1$, and $X_3$, if it forms a ring with $C_1$, is defined like $X_1$ and, if it does not form a ring with $C_1$, corresponds to a group

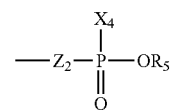

wherein $R_5$ is defined like $R_3$, and $Z_2$ and $X_4$, which forms a ring with Cl, are defined like $X_1$.

Particular preference is given to compounds having formula (IIA)

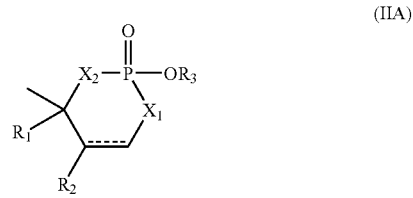
(IIA)

wherein $C_2$ and $C_3$ are linked together by either a single or a double bond, $R_1$ is a methyl group or a substituted or unsubstituted hydroxymethyl group, $R_2$ is hydrogen, OH, a substituted or unsubstituted phosphate or a substituted or unsubstituted pyrophosphate, $X_1$ and $X_2$ are selected from the group comprising O, CHF, CHCl, CFCl, $CH_2$, $CF_2$ or $CCl_2$, and $R_3$ is selected from the group comprising hydrogen, substituted and unsubstituted phosphate, a nucleoside, a nucleoside mono-, di- or triphosphate, a deoxynucleoside, a cation of an organic or inorganic base, particularly a metal of the first, second or third main group of the Periodic Table, ammonium, substituted ammonium and ammonium compounds derived from ethylenediamine or amino acids.

Preference is also given to compounds having formula (IIB)

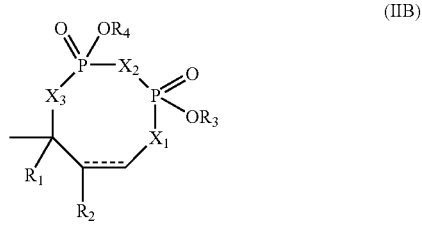
(IIB)

wherein $C_2$ and $C_3$ are linked together by either a single bond or a double bond, $R_1$ is a methyl group or a substituted or unsubstituted hydroxymethyl group, $R_2$ is H if $R_1$ is a substituted or unsubstituted hydroxymethyl and is OH, a substituted or unsubstituted phosphate or a substituted or unsubstituted pyrophosphate if $R_1$ is a methyl residue, $X_1$, $X_2$ and $X_3$ are selected from the group comprising O, CHF, CHCl, CFCl, $CH_2$, $CF_2$ or $CCl_2$, and $R_3$ and $R_4$ are selected from the group comprising hydrogen, substituted and unsubstituted phosphate, a nucleoside, a nucleoside mono-, di- or triphosphate, a deoxynucleoside, a cation of an organic or inorganic base, particularly a metal of the first, second or third main group of the Periodic Table, ammonium, substituted ammonium and ammonium compounds derived from ethylenediamine or amino acids.

Preference is likewise given to compounds having formula (IIC)

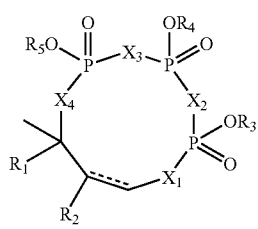

wherein a single or double bond can be present between $C_2$ and $C_3$, $R_1$ is a methyl or a substituted or unsubstituted hydroxymethyl group, $R_2$ is H, OH, a substituted or unsubstituted phosphate or a substituted or unsubstituted pyrophosphate, $X_1$, $X_2$, $X_3$ and $X_4$ are selected from the group comprising O, CHF, CHCl, CFCl, $CH_2$, $CF_2$ or $CCl_2$, and $R_3$, $R_4$ and $R_5$ are selected from the group comprising hydrogen, substituted or unsubstituted phosphate, a nucleoside, a nucleoside mono-, di- or triphosphate, a deoxynucleoside, a cation of an organic or inorganic base, particularly a metal of the first, second or third main group of the Periodic Table, ammonium, substituted ammonium and ammonium compounds derived from ethylenediamine or amino acids.

Moreover, preferred compounds having formulae (II) and (IIA) to (IIC) are those wherein $R_1$ is a substituted or unsubstituted hydroxymethyl residue, particularly hydroxymethyl itself or a hydroxymethyl residue substituted by phosphate, diphosphate or nucleoside diphosphate, for example a hydroxymethyl residue substituted by uridine diphosphate, and $R_2$=H.

Compounds which are likewise preferred are those having formulae (II) and (IIA) to (IIC) in which $R_1$ is a methyl residue and $R_2$ is a hydroxyl residue, a substituted or unsubstituted phosphate residue or a substituted or unsubstituted diphosphate residue, particularly a nucleoside diphosphate residue, e.g. a uridine diphosphate residue.

The following compounds are particularly preferred:

1
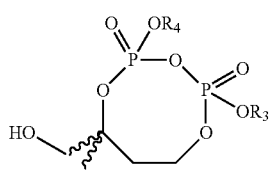

2
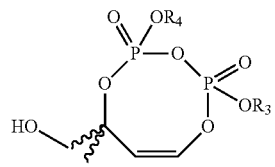

3
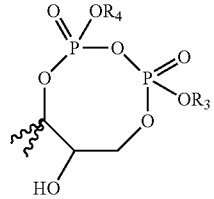

4
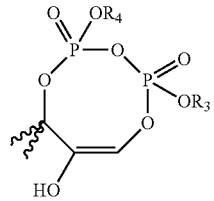

5
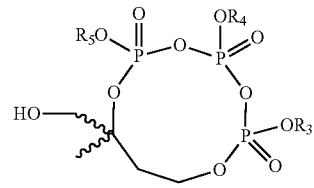

6
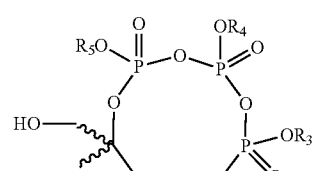

7
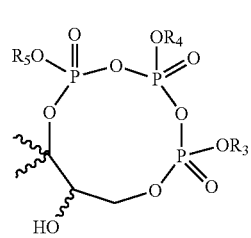

8
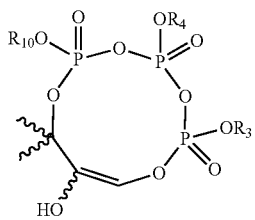

wherein the residues $R_3$, $R_4$ and $R_5$ are selected from the group comprising hydrogen, ammonium, sodium or potassium.

Furthermore, preferred compounds also include those having the following formula:

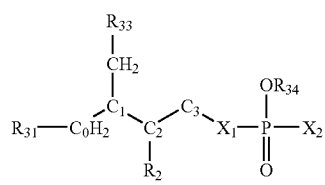
(III)

wherein $R_{31}$ and $R_2$, which cannot both be present in the molecule at the same time, are selected from the group comprising OH, substituted and unsubstituted phosphate and substituted and unsubstituted pyrophosphate; if $R_{31}$ is present in the molecule, a double bond is formed between $C_1$ and $C_2$, and a double bond is analogously formed between $C_0$ and $C_1$ if $R_2$ is present in the molecule; $R_{33}$ is selected from the group comprising hydrogen, OH, substituted and unsubstituted phosphate and substituted and unsubstituted pyrophosphate; $R_{34}$ is selected from the group comprising hydrogen, substituted or unsubstituted alkyl with 1 to 26 carbon atoms, substituted or unsubstituted hydroxyalkyl with 1 to 26 carbon atoms, substituted or unsubstituted aryl, substituted or unsubstituted aralkyl, substituted or unsubstituted alkenyl with 1 to 26 carbon atoms, substituted or unsubstituted alkinyl with 1 to 26 carbon atoms, substituted or unsubstituted cycloalkyl, a substituted or unsubstituted heterocyclic residue, substituted or unsubstituted phosphate, a silyl, a nucleoside, a deoxynucleoside, a nucleoside mono-, di- or triphosphate, a cation of an organic or inorganic base, particularly a metal of the first, second or third main group of the Periodic Table, ammonium, substituted ammonium or ammonium compounds derived from ethylenediamine or amino acids; $X_2$ is either $-OR_6$, wherein $R_6$ is defined analogously to $R_{34}$, or may be

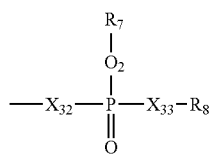

wherein $R_7$ and $R_8$ are defined like $R_{34}$; and $X_1$, $X_{32}$ and $X_{33}$ can be the same or can be different and can be oxygen or a group

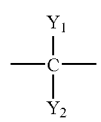

wherein $Y_1$ and $Y_2$ can be the same or can be different and are selected from the group comprising H, OH, halogen, an amino residue, a $C_{1-9}$-alkoxy residue and a $C_{1-9}$-alkylthio residue, or together form an oxo group.

Particularly preferred compounds are those having formula (IIIA)

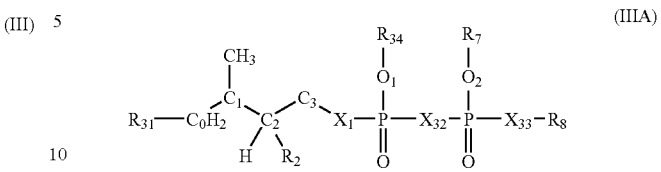
(IIIA)

wherein $R_{31}$ and $R_2$, which cannot be present in the molecule at the same time, are selected from the group comprising OH, substituted and unsubstituted phosphate and substituted and unsubstituted pyrophosphate; if $R_{31}$ is present in the molecule, a double bond is formed between $C_1$ and $C_3$, and a double bond is formed analogously between $C_0$ and $C_1$ if $R_2$ is present in the molecule; $R_{34}$, $R_7$ and $R_8$ can be the same or can be different and are defined as above; and $X_1$, $X_{32}$ and $X_{33}$ can be the same or can be different and are defined as for compound (III).

Hydrogen substituents at $C_1$, $C_2$ and $C_3$ are not explicitly indicated in formulae (I) to (IIIA) for reasons of clarity. However, carbon atoms are understood as being tetravalent. The missing substituents are therefore hydrogen radicals.

Furthermore, preference is given to compounds having formula (IIIA) in which $R_{31}$ and $R_2$ are either OH or substituted or unsubstituted phosphate, $R_{34}$, $R_7$ and $R_8$ are selected from the group comprising substituted and unsubstituted phosphate, a nucleoside, a deoxynucleoside, a nucleoside mono-, di- or triphosphate, a cation of an organic or inorganic base, particularly a metal of the first, second or third main group of the Periodic Table, ammonium, substituted ammonium and ammonium compounds derived from ethylenediamine or amino acids, and $X_1$, $X_{32}$ and $X_{33}$ can be the same or can be different and are O, CHF, CHCl, CFCl, $CH_2$, $CF_2$ or $CCl_2$.

Other preferred compounds having formula (IIIA) are those in which the phosphate groups are present as sodium, potassium or substituted or unsubstituted ammonium salts.

The following compounds are most suitable:

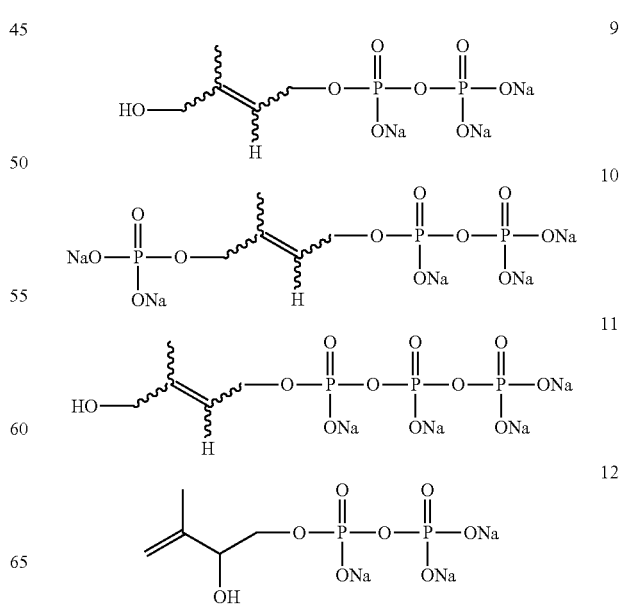

-continued

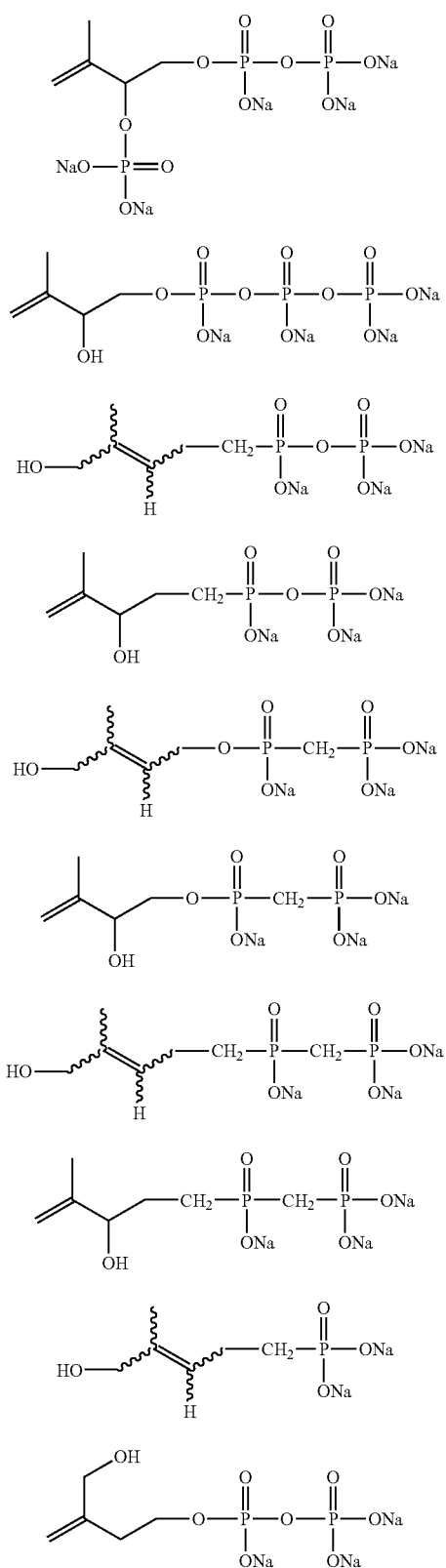

Other embodiments of the invention are defined by the subordinate claims.

Peculiarities of the abovementioned definitions and suitable Examples of these will be given below:

"Alkyl" is a straight-chain or branched-chain alkyl residue with up to 26 carbon atoms, unless otherwise stated, such as methyl, ethyl, propyl, isopropyl, butyl, isobutyl, tert-butyl, pentyl, hexyl and the like.

Unless otherwise stated, "alkenyl" includes straight-chain or branched-chain alkenyl groups with up to 26 carbon atoms, e.g. vinyl, propenyl (e.g. 1-propenyl, 2-propenyl), 1-methylpropenyl, 2-methylpropenyl, butenyl, 2-ethylpropenyl, pentenyl and hexenyl.

Unless otherwise stated, "alkinyl" includes straight-chain or branched-chain alkinyl groups with up to 26 carbon atoms.

Cycloalkyl preferably refers to a $C_3$-$C_7$-cycloalkyl that may be substituted; alkyl, alkoxy (e.g. methoxy, ethoxy, etc.), halogen (e.g. fluorine, chlorine, bromine, etc.), nitro and the like are suitable as possible substituents.

Aryl is an aromatic hydrocarbon residue, such as phenyl, naphthyl, etc., which may have one or more suitable substituents such as alkoxy (e.g. methoxy, ethoxy, etc.), halogen (e.g. fluorine, chlorine, bromine, etc.), nitro and the like.

"Aralkyl" includes mono-, di- and triphenylalkyls such as benzyl, phenethyl, benzhydryl, trityl and the like, where the aromatic part may have one or more suitable substituents such as alkoxy (e.g. methoxy, ethoxy, etc.), halogen (e.g. fluorine, chlorine, bromine, etc.), nitro and the like.

"Alkoxy residue" relates to a straight-chain or branched-chain alkoxy residue with up to 26 carbon atoms, such as methoxy or ethoxy residues, etc., unless otherwise stated. It can be substituted for example by hydroxyl, amino, halogen and oxo groups and alkoxy residues such as methoxy or ethoxy residues.

Unless otherwise stated, "hydroxymethyl residue" relates to a residue that has a substituted or unsubstituted $C_1$-$C_9$-alkyl, aryl or aralkyl residue, e.g. methoxymethyl, ethoxymethyl, phenoxymethyl or benzoxymethyl, etc., attached to the oxygen, or has a substituted or unsubstituted phosphate or pyrophosphate residue, such as adenosine diphosphate, uridine diphosphate, etc., attached to the oxygen.

Unless otherwise stated, "alkylthio residue" relates to a straight-chain or branched-chain alkylthio residue with up to 9 carbon atoms, such as thiomethyl or thioethyl residues, etc. It can be substituted e.g. by hydroxyl, amino, halogen and oxo groups and alkoxy residues such as methoxy or ethoxy residues.

"Silyl residues" can, for example, be substituted by the above-defined alkyl residues or cycloalkyl-($C_{0-26}$)-alkyl residues.

"Silyl-($C_{0-26}$)-alkyl groups" are silyl residues that can also be bonded to the framework by means of an alkyl residue. The alkyl and silyl groups are defined as above.

The alkane and/or arene parts may, if desired, have at least one suitable substituent such as a halogen, alkoxy, hydroxyl, nitro or the like, in the case of the aforementioned esters.

Substituted and unsubstituted phosphate residues or substituted and unsubstituted pyrophosphate residues include salt compounds of the corresponding phosphoric acid derivatives with organic or inorganic bases (e.g. sodium salt, potassium salt, calcium salt, aluminium salt, ammonium salt, magnesium salt, triethylamine salt, ethanolamine salt, dicyclohexylamine salt, ethylenediamine salt, N,N'-dibenzylethylenediamine salt, etc.), as well as amino acid salts (e.g. arginine salt, lysine salt, glycine salt, alanine salt, ornithine salt, etc.), and also residues in which the phosphate group forms esters with substituted or unsubstituted $C_1$-$C_{26}$-alkyl, substituted or unsubstituted aryl, substituted or unsubstituted aralkyl, substituted or unsubstituted cycloalkyl or a substituted or unsubstituted heterocyclic residue, or with a nucleoside or a deoxynucleoside.

"Nucleoside" is understood as meaning adenosine, guanosine, uridine, thymidine and cytidine, while "deoxynucleoside" is understood as meaning deoxyadenosine, deoxyguanosine, deoxythymidine, deoxycytidine and deoxyuridine.

The invention also relates to the pharmaceutical salts and esters of the salts. Moreover, it includes all spatial isomers of the compounds, both as pure substances and as mixtures thereof.

The substances according to the invention can be obtained from bacteria, algae, plants and protozoa, including those in which the lytB gene has been deleted, and purified (Example 1). Purification can be effected by means of HPLC or by other methods known per se, such as electrophoresis, precipitation (e.g. as a barium salt) or other chromatographic techniques.

Various applications of the compounds are possible. Accordingly, it has been shown, for example, that the substances can be employed in the activity testing of the enzymes GcpE and LytB, as well as in test systems for the measurement of gamma/delta T-cell activation (see Examples 2, 5).

The substances according to the invention can either be chemically synthesized (Example 3) or be obtained from bacteria, algae, plants and protozoa and purified (Example 4). Purification can be effected by means of HPLC or by other methods known per se, such as electrophoresis, precipitation (e.g. as a barium salt) or other chromatographic techniques.

Furthermore, the substances according to the invention can be used in a screening procedure for the identification of GcpE and LytB enzyme inhibitors, as they are intermediates of the MEP. This method of determining the activity of the enzymes is based on the measurement of differences in the concentration of the enzyme substrates and products under suitable reaction conditions. By bringing suitable test substances into contact with the enzymes during activity determination, inhibitors can be identified by the reduction in the observed enzyme activity. The inhibitors are suitable as herbicides and as active ingredients with antibacterial, antiparasitic and antiviral activity in humans and animals.

The compounds according to the invention can also be used in the production of medicines. The efficacy of the compounds is based on the activation of gamma/delta T-cells. Depending on the field of application, the immunological defence mechanism can thereby be strengthened or an immunological tolerance can be induced towards autoantigens and allergens.

The fields of application are the treatment of immune and autoimmune diseases and allergies in humans and animals. Examples of these are: allergies, multiple sclerosis, rheumatoid arthritis, Hashimoto's thyroiditis, myasthenia gravis, lupus erythematosus, diabetes mellitus, primary biliary cirrhosis, active chronic hepatitis, adrenalitis/Addison's disease, polymyositis, dermatomyositis, autoimmune haemolytic anaemia, myocardial inflammation and inflammation of the heart membrane, scleroderma, uveitis (phacouveitis, sympathetic ophthalmia), pemphigus vulgaris, pemphigoid, pernicious anaemia, autoimmune atrophic gastritis, inflammatory diseases of the intestine, such as Crohn's disease and ulcerative colitis, and inflammatory diseases of the lung, such as asthmatic and bronchitic ailments.

The preferred fields of application are Crohn's disease, ulcerative colitis, multiple sclerosis, asthma, chronic bronchitis and allergies.

Furthermore, it has been shown that the substances according to the invention can be successfully employed in the treatment of diseases which are caused by viruses, bacteria and parasites.

In particular, the substances defined in claim 1 and the subordinate claims are suitable for the prevention and treatment of tumours that are caused by microorganisms. Bacteria, such as *Helicobacter pylori* (e.g. tumours of the gastrointestinal tract), and papilloma viruses (e.g. tumours of the female genitalia), belong to this group of microorganisms.

The compounds defined in the claims are particularly suitable for the prophylaxis and treatment of one of the aforesaid diseases as well as hepatitis C virus infections and benign and malignant tumours, particularly those caused by papilloma viruses, and for helicobacter eradication therapy in cases of ulceration of the gastrointestinal tract.

For medicinal purposes, pharmaceutical preparations can be used on their own or in combination with other medicines and can contain either the isolated substances according to the invention or living or dead organisms containing the substances. They are preferably used in combination with substances that are recognized by the immune system as being foreign antigens or autoantigens.

Examples of these are myelin basic protein (MBP) and other extracts of the tissue of the nervous system, type I, II or III collagen, thyroglobulin, acetylcholine receptor protein, DNA, islet cell extracts, human insulin, liver extracts, hepatocellular extracts, adrenocortical extracts, skin extracts, heart extracts, muscle extracts, skin cell extracts, haemopoietic line cell extracts, eye lens proteins, S-antigens, S-antigen mixtures, stomach cell extracts, parietal cell extracts, intrinsic factor and intestinal extracts.

Preferred forms of administration are oral, inhalational, intravenous, parenteral, intracisternal, intravaginal, intraperitoneal, local (powder, ointment, drops) and rectal administration, as well as application to the skin or mucous membranes.

The invention includes the administration of an inhalant containing at least one of the substances defined in claim 1 for the treatment of human diseases, particularly allergies and diseases of the respiratory tract such as asthma and chronic bronchitis.

Suitable pharmaceutical compositions are moreover: tablets, retard tablets, dragees, capsules, premixes, pills, pellets, boli, aerosols, granules, suppositories, solutions, concentrates, suspensions and emulsions, pastes, ointments, gels, creams, lotions, powders, infusions and sprays. The pharmaceutical formulations may correspond to a fraction or a multiple of a single dose. Dosage units can be 1, 2, 3 or 4 times a single dose, for example, or may contain ½, ⅓ or ¼ of a single dose. A single dose preferably contains the quantity of active ingredient which is used for one administration and which usually corresponds to a whole, a half, a third or a quarter of the daily dosage.

Tablets, dragees, capsules, pills and granules may contain the active ingredients in addition to the usual excipients such as (a) fillers and diluents, e.g. starches, lactose, cane sugar, glucose, mannitol and silicic acid, (b) binders, e.g. carboxymethyl cellulose, alginates, gelatine and polyvinylpyrrolidone, (c) humectants, e.g. glycerine, (d) disintegrating agents, e.g. agar-agar, calcium carbonate and sodium carbonate, (e) solution retarders, e.g. paraffin, and (f) absorption accelerators, e.g. quaternary ammonium compounds, (g) wetting agents, e.g. cetyl alcohol and glycerol monostearate, (h) adsorbents, e.g. kaolin and bentonite, and (i) lubricants, e.g. talcum, calcium and magnesium stearate and solid polyethylene glycols, or mixtures of the substances listed under (a) to (i). Moreover, the compounds according to the invention can also be incorporated into other carrier materials such as plastics (plastic chains for local therapy), collagen or bone cement.

The tablets, dragees, capsules, pills and granules may be provided with the usual coatings and envelopes optionally containing opaquing agents, and can be prepared in such a way that the active ingredients are released, optionally with a delay, only in the intestinal tract or, preferably, in a particular part of the intestinal tract, it being possible to use e.g. polymer substances and waxes as embedding compounds.

The active ingredients can also be in microencapsulated form, optionally with one or more of the aforesaid excipients.

In addition to the active ingredients, suppositories may contain the usual water-soluble or water-insoluble excipients, e.g. polyethylene glycols, fats, e.g. cacao fat, and higher esters (e.g. a $C_{14}$ alcohol with a $C_{16}$ fatty acid), or mixtures of these substances.

In addition to the active ingredient(s), ointments, pastes, creams and gels can contain the usual excipients, e.g. animal and vegetable fats, waxes, paraffins, starch, tragacanth, cellulose derivatives, polyethylene glycols, silicones, bentonites, silicic acids, talcum and zinc oxide, or mixtures of these substances.

In addition to the active ingredient(s), powders and sprays may contain the usual excipients, e.g. lactose, talcum, silicic acid, aluminium hydroxide, calcium silicate and polyamide powder, or mixtures of these substances. Additionally, sprays may also contain the usual propellant, e.g. chlorofluorocarbons.

In addition to the active ingredients, solutions and emulsions may contain the usual excipients such as solvents, solubilizers and emulsifying agents, e.g. water, ethyl alcohol, isopropyl alcohol, ethyl carbonate, ethyl acetate, benzyl alcohol, benzyl benzoate, propylene glycol, 1,3-butylene glycol, dimethylformamide, oils, particularly cottonseed oil, peanut oil, maize oil, olive oil, castor oil and sesame oil, glycerine, glycerol formal, tetrahydrofurfuryl alcohol, polyethylene glycols and fatty acid esters of sorbitol, or mixtures of these substances.

There are very marked differences in the amounts of the individual derivatives that are necessary in order to achieve the desired effect. Generally speaking, both in human as well as in veterinary medicine, it has proved to be advantageous if the active ingredient(s) of formula (I) are administered in total amounts of approximately 0.01 to about 2000 μg every 24 hours, if necessary in the form of several single doses, in order to achieve the desired results. A single dose preferably contains the active ingredient(s) in amounts of approximately 0.01 to about 2000 μg. However, it may be necessary to deviate from the abovementioned dosages, depending on the type and body weight of the person to be treated, the nature and severity of the disease, the type of preparation and the administration of the medicine, as well as the period or interval over which the preparation is administered.

Consequently, it may be sufficient in a number of cases to manage with less than the abovementioned quantity of active ingredient, while in other cases the aforementioned quantity of active ingredient will have to be exceeded. The optimum dosage required and the type of administration of the active ingredients can be determined by those skilled in the art on the basis of their specialist knowledge.

In the treatment of animals, the compounds to be used according to this invention can be given in the usual concentrations and preparations together with the food or food preparations or with the drinking water.

EXAMPLE 1

Purification of Gamma/Delta T-Cell Activating Compounds

Various gamma/delta T-cell activating compounds were isolated from Coryne-bacterium ammoniagenes. 28 kg of the cell mass were digested with a Dynax mill in 50 mM ammonium formate buffer (pH 8.0). After preabsorption on a hydrophobic polystyrene matrix, the digested material was loaded onto an anion exchanger and eluted with a stepped gradient (100, 300, 500 mM ammonium formate, pH 8.0). The 300 mM eluate was passed through a C-18 matrix and then through a 3 kDa hollow fibre filter for ultrafiltration. The filtrate was diluted with water to 30 mM ammonium formate and loaded once more onto an anion exchanger. Elution then took place with a linear gradient of 30 to 500 mM ammonium formate. Individual fractions were tested for their ability to activate gamma/delta T-cells. Then some of the active compounds were precipitated as barium salts by the admixture of 100 mM $BaCl_2$ and 80% EtOH. The precipitates were dissolved in 20 mM ammonium formate buffer (pH 8.0) and rechromatographed on an anion exchanger.

In this way it is possible to isolate compounds 1 to 6.

EXAMPLE 2

Activation of Gamma/Delta T-Cells by Enriched MEP Intermediates

Lymphocytes were obtained from the peripheral blood of healthy donors by Ficoll density gradient centrifugation. For each test, $2 \times 10^5$ of the cells so obtained were seeded in a volume of 0.2 ml of RPMI-1640 medium (Life Technologies) that was enriched with 25 mM HEPES, 2 mM L-glutamine, 0.025 mg/ml of gentamicin, 100 U/ml of human interleukin-2 (IL-2) (all from Life Technologies) and 10% human AB serum (Bavarian Red Cross). The test fractions were added in various dilutions, and isopentenyl diphosphate (IPP) from Sigma was used in a final concentration of 10 μM as a positive control. Incubation was effected in the incubator with 5% $CO_2$ at 37° C. After 72 hours the cells were harvested and analysed in a flow cytometer. In so doing, the expression of the CD25 activation marker on the surface of V gamma $9^+$ T-cells was measured with the aid of the monoclonal antibodies CD25-PE (B1.49.9), V gamma 9-FITC (Immu360) and CD3-PC5 (UCHT1) supplied by Beckman-Coulter.

The results showed that compound 1 was approximately 750 times more active than IPP, while compound 2 was about 400 times and compounds 3, 5 and 6 were about 100 times more active than IPP.

EXAMPLE 3

The synthesis was effected in the manner described in diagram 1:

Diagram 1: Synthesis plan

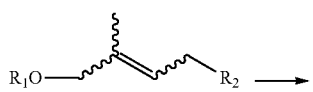

Ia: $R_1$ = benzyl; $R_2$ = OH
Ib: $R_1$ = benzyl; $R_2$ = Br

Ic: $R_1$ = acetyl; $R_2$ = Br

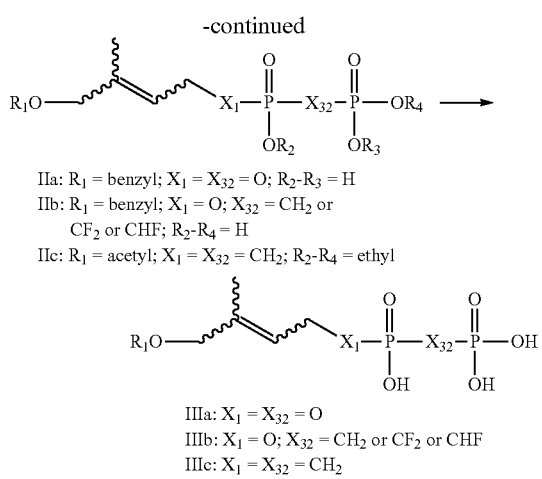

IIa: $R_1$ = benzyl; $X_1 = X_{32}$ = O; $R_2$-$R_3$ = H
IIb: $R_1$ = benzyl; $X_1$ = O; $X_{32}$ = $CH_2$ or $CF_2$ or CHF; $R_2$-$R_4$ = H
IIc: $R_1$ = acetyl; $X_1 = X_{32}$ = $CH_2$; $R_2$-$R_4$ = ethyl IIIa: $X_1 = X_{32}$ = O
IIIb: $X_1$ = O; $X_{32}$ = $CH_2$ or $CF_2$ or CHF
IIIc: $X_1 = X_{32}$ = $CH_2$ 1. Preparation of compounds Ia to Ic Compounds Ia and Ib were prepared in an analogous manner to that described in K. Sato, S. Inoue, Y. Takagi, S. Morii, Bull. Chem. Soc. Jpn., 1976, 49(11), 3351-3351.

The preparation of compound Ic is analogous to that described in H. Kunio, H. Kazushige, Chem. Pharm. Bull., 1994, 42, 4, 786-791.

2. Syntheses of Compounds IIa to IIc

Compound IIa was prepared according to current methods which are known to those skilled in the art, such as have been described in e.g. B. Woodside, Z. Huang, C. Poulter, Org. Synth. 1989, 66, 211-219, starting from compound Ib.

Compound IIb was prepared starting from compound Ia. Ia was first converted to the corresponding tosylate and then reacted e.g. with tris(tetra-n-butylammonium) hydrogenomethylenediphosphate. The synthesis was carried out in a manner analogous to that described in WO00/59916 and the publications cited therein.

Compound IIc in turn was prepared from -compound Ic. The syntheses were carried out in the manner described in R. C. McClard and T. S. Fujita, J. Am. Chem. Soc., 1987, 109, 5544-5545.

Compound IIc could be obtained in a low yield and was immediately hydrolysed in order to obtain compound IIIc.

3. Syntheses of Compounds IIIa to IIIc

In order to prepare compounds IIIa to IIIc, 500 mg of the corresponding precursors IIa and IIb were each dissolved in 5 ml of methanol and treated with 10 mol % of hydrogenation catalyst. Then hydrogen was introduced at room temperature and the uptake of hydrogen was measured. After the appropriate amount of hydrogen had been taken up, the mixture was filtered and the solvent was stripped off. The required products IIIa and IIIb were obtained with a good degree of purity. Further purification can be achieved by chromatographic methods. Compound IIIc was obtained from compound IIc. 200 mg of compound IIc were dissolved in absolute methylene chloride (3 ml) in a heated, argon-flushed flask and 10 eq. of trimethylbromosilane were added at 0° C. After stirring for one hour at 0° C., stirring was continued for a further 12 h at room temperature. Finally, an aqueous work-up yielded the required product IIIc, which was purified by ion exchange chromatography.

In order to test the activation of gamma/delta T-cells, either the isomerically pure compounds or E/Z mixtures of the compounds were used.

EXAMPLE 4

Purification of Gamma/Delta T-Cell Activating Compounds

Various gamma/delta T-cell activating compounds were isolated from Coryne-bacterium ammoniagenes. 28 kg of the cell mass were digested with a Dynax mill in 50 mM ammonium formate buffer (pH 8.0). After preabsorption on a hydrophobic polystyrene matrix, the digested material was loaded onto an anion exchanger and eluted with a stepped gradient (100, 300, 500 mM ammonium formate, pH 8.0). The 300 mM eluate was passed through a C-18 matrix and then through a 3 kDa hollow fibre filter for ultrafiltration. The filtrate was diluted with water to 30 mM ammonium formate and loaded once more onto an anion exchanger. Elution then took place with a linear gradient of 30 to 500 mM ammonium formate. Individual fractions were tested for their ability to activate gamma/delta T-cells. Then some of the active compounds were precipitated as barium salts by the admixture of 100 mM $BaCl_2$ and 80% EtOH. The precipitates were dissolved in 20 mM ammonium formate buffer (pH 8.0) and rechromatographed on an anion exchanger. In this way it was possible to isolate compounds 1 to 6, 13 and 14.

EXAMPLE 5

Activation of Gamma/Delta T-Cells by Enriched MEP Intermediates

Lymphocytes were obtained from the peripheral blood of healthy donors by Ficoll density gradient centrifugation. For each test, $2 \times 10^5$ of the cells so obtained were seeded in a volume of 0.2 ml of RPMI-1640 medium (Life Technologies) that was enriched with 25 mM HEPES, 2 mM L-glutamine, 0.025 mg/ml of gentamicin, 100 U/ml of human interleukin-2 (IL-2) (all from Life Technologies) and 10% human AB serum (Bavarian Red Cross). The test fractions were added in various dilutions, and isopentenyl diphosphate (IPP) from Sigma was used in a final concentration of 10 μM as a positive control. Incubation was effected in the incubator with 5% $CO_2$ at 37° C. After 72 hours the cells were harvested and analysed in a flow cytometer. In so doing, the expression of the CD25 activation marker on the surface of V gamma $9^+$ T-cells was measured with the aid of the monoclonal antibodies CD25-PE (B1.49.9), V gamma 9-FITC (Immu360) and CD3-PC5 (UCHT1) supplied by Beckman-Coulter.

The results showed that compound 9 was approximately 10,000 times more active than IPP, compounds 15, 17 and 19 were about 500 times more active, compound 10 was around 1000 times more active and compound 12 was about 50 times more active than IPP.

The invention claimed is:

1. A pharmaceutical composition comprising between approximately 0.01 to about 2000 μg of a compound of general formula (III):

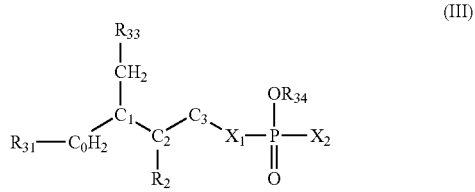

in which $R_{31}$ and $R_2$, which cannot be present in the molecule simultaneously, are selected from the group consisting of OH, substituted or unsubstituted phosphate and substituted or unsubstituted pyrophosphate, a double bond is present between $C_1$ and $C_2$ if $R_{31}$ is present in the molecule and a double bond is present between $C_0$ and $C_1$ if $R_2$ is present in the molecule, $R_{33}$ is selected from the group consisting of hydrogen, OH, substituted or unsubstituted phosphate and substituted or unsubstituted pyrophosphate, $R_{34}$ is selected from the group consisting of hydrogen, substituted or unsubstituted alkyl having 1 to 26 carbon atoms, substituted or unsubstituted hydroxyalkyl having 1 to 26 carbon atoms, substituted or unsubstituted aryl, substituted or unsubstituted aralkyl, substituted or unsubstituted alkenyl having 1 to 26 carbon atoms, substituted or unsubstituted alkynyl having 1 to 26 carbon atoms, substituted or unsubstituted cycloalkyl, substituted or unsubstituted heterocyclic radicals, substituted or unsubstituted phosphate, a silyl, a nucleoside, a deoxynucleoside, a nucleoside monophosphate, diphosphate or triphosphate, a cation of an organic or inorganic base, a cation of an organic or inorganic base wherein the metal is from main group I, II or III of the Periodic Table, ammonium, substituted ammonium and ammonium compounds derived from ethylenediamine or amino acids, $X_2$ is either —$OR_6$, $R_6$ being defined analogously to $R_{34}$, or can be

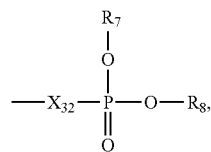

$R_7$ and $R_8$ are independently selected from the group consisting of hydrogen, substituted or unsubstituted alkyl having 1 to 26 carbon atoms, substituted or unsubstituted hydroxyalkyl having 1 to 26 carbon atoms, substituted or unsubstituted aryl, substituted or unsubstituted aralkyl, substituted or unsubstituted alkenyl having 1 to 26 carbon atoms, substituted or unsubstituted alkynyl having 1 to 26 carbon atoms, substituted or unsubstituted cycloalkyl, substituted or unsubstituted heterocyclic radicals, substituted or unsubstituted phosphate, a silyl, a nucleoside, a nucleoside monophosphate, diphosphate or triphosphate, a deoxynucleoside, a cation of an organic or inorganic base, a cation of an organic or inorganic base wherein the metal is from main group I, II or III of the Periodic Table, ammonium, substituted ammonium, ammonium compounds derived from ethylenediamine or amino acids, and $OR_{34}$, and $X_1$, $X_{32}$ and $X_{33}$, which can be identical or different, can be oxygen or a group

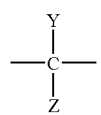

Y and Z, which can be identical or different, being selected from the group consisting of H, halogen, amino, $C_{1-9}$-alkoxy and $C_{1-9}$-alkylthio, or together forming an oxo group, or one of its pharmaceutical salts or esters of the salt.

2. The pharmaceutical composition according to claim 1 comprising the compound of general formula (IIIA):

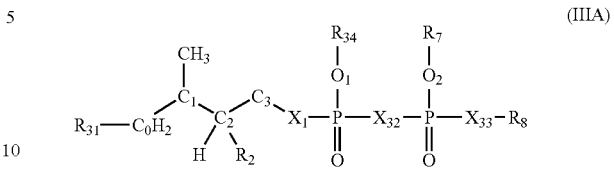

in which $R_{31}$ and $R_2$, which cannot be present in the molecule simultaneously, are selected from the group consisting of OH, substituted or unsubstituted phosphate and substituted or unsubstituted Pyrophosphate, a double bond is present between $C_1$ and $C_2$ if $R_{31}$ is present in the molecule and a double bond is present between $C_0$ and $C_1$ if $R_2$ is present in the molecule, $R_{34}$, $R_7$ and $R_8$, which can be identical or different, and $X_1$, $X_{32}$ and $X_{33}$, which can be identical or different, are as defined in claim 1.

3. The pharmaceutical composition according to claim 1 in which $R_{31}$=OH and $C_1$ and $C_2$ are joined by a double bond.

4. The pharmaceutical composition according to claim 1 in which $R_2$=OH and $C_0$ and $C_1$ are joined by a double bond.

5. The pharmaceutical composition according to claim 1, wherein either $R_{34}$ or $R_6$ or $R_7$ or $R_8$ is a substituted or unsubstituted phosphate radical.

6. The pharmaceutical composition according to claim 1, wherein either $R_{31}$ or $R_2$ or $X_2$ is a substituted or unsubstituted phosphate radical.

7. The pharmaceutical composition according to claim 1, wherein $R_{34}$, $R_6$, $R_7$ and $R_8$, which can be identical or different, are hydrogen, a cation of a metal of main group I, II or III of the Periodic Table, or substituted or unsubstituted ammonium.

8. The pharmaceutical composition according to claim 1, wherein $X_1$ and $X_{32}$=O.

9. The pharmaceutical composition according to claim 1, wherein $X_1$=CYZ, $X_{32}$=O and $X_{33}$=CYZ, Y and Z being as defined in claim 1.

10. The pharmaceutical composition according to claim 1, wherein $X_1$=O, $X_{32}$=CYZ and $X_{33}$=O, Y and Z being as defined in claim 1.

11. The pharmaceutical composition according to claim 1, wherein $X_1$, $X_{32}$ and $X_{33}$, which can be identical or different, are selected from the group consisting of $CH_2$, CHF, CHCl, CFCl, $CCl_2$ and $CF_2$.

12. The pharmaceutical composition according to claim 1 selected from the following group:

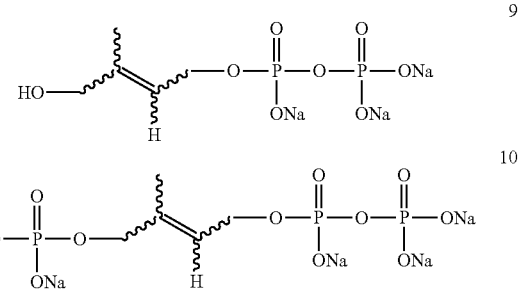

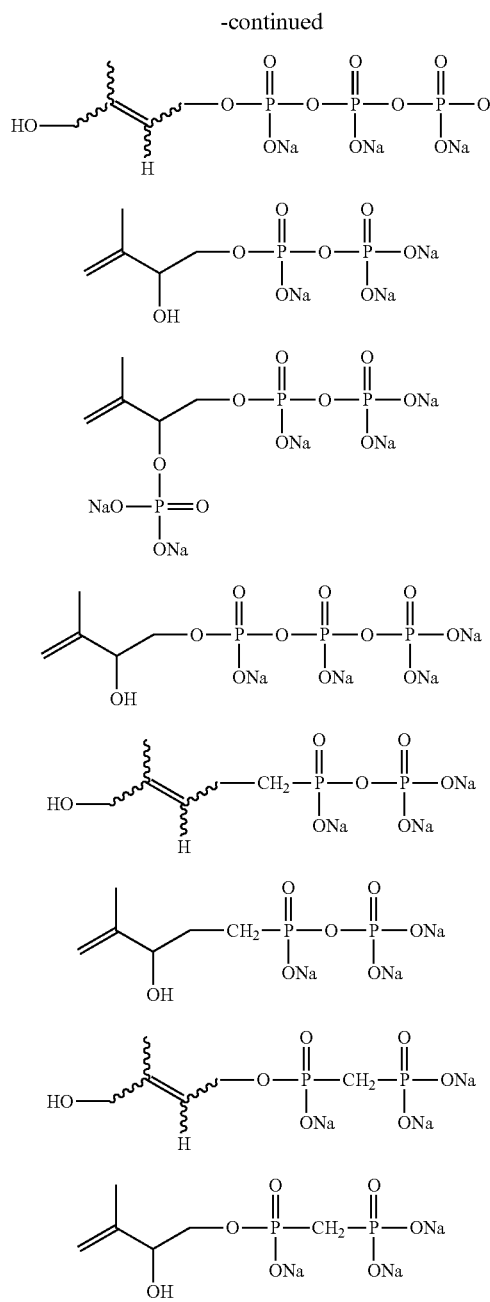

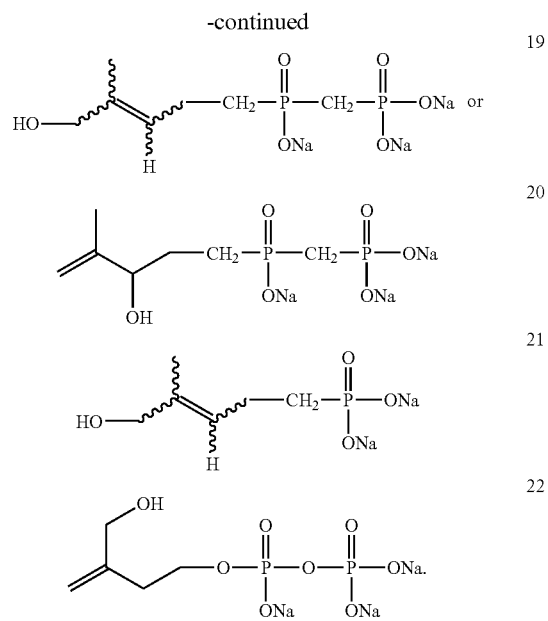

13. The pharmaceutical composition according to claim 1 wherein said composition is a tablet, retard tablet, dragee, capsule, premixe, pill, pellet, bolus, aerosol, granule, suppository, solution, concentrate, suspension, emulsion, paste, ointment, gel, cream, lotion, powder, infusion or spray.

14. The pharmaceutical composition according to claim 13, wherein said composition comprises one or more excipient selected from the group consisting of:
 a. fillers and diluents;
 b. binders;
 c. humectants;
 d. disintegrating agents;
 e. solution retarders;
 f. absorption accelerators;
 g. wetting agents;
 h. adsorbents;
 i. lubricants; and
 j. mixtures thereof.

15. The pharmaceutical composition according to claim 1, wherein said compound is microencapsulated.

16. The pharmaceutical composition according to claim 1, wherein said composition further comprises an antigen.

* * * * *

UNITED STATES PATENT AND TRADEMARK OFFICE
CERTIFICATE OF CORRECTION

| | | |
|---|---|---|
| PATENT NO. | : 7,871,992 B2 | Page 1 of 2 |
| APPLICATION NO. | : 12/137241 | |
| DATED | : January 18, 2011 | |
| INVENTOR(S) | : Hassan Jomaa et al. | |

It is certified that error appears in the above-identified patent and that said Letters Patent is hereby corrected as shown below:

Column 2,
Line 50, "and $Z_7$" should read --and $Z_1$--.

Column 4,
Line 23, "with C1" should read --with $C_1$--.

Column 15,
Line 8, "$R_2$-$R_3$ = H" should read --$R_2$-$R_4$ = H--.
Line 33, "1989" should read --1988--.

Column 17,
Line 35,

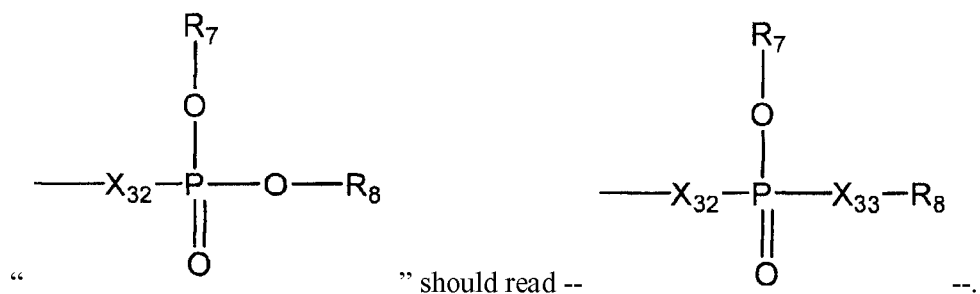

Line 65, "H, halogen," should read --H, OH, halogen,--.

Signed and Sealed this
Fifth Day of April, 2011

David J. Kappos
*Director of the United States Patent and Trademark Office*

CERTIFICATE OF CORRECTION (continued)
U.S. Pat. No. 7,871,992 B2

Column 20,
Line 5,

"

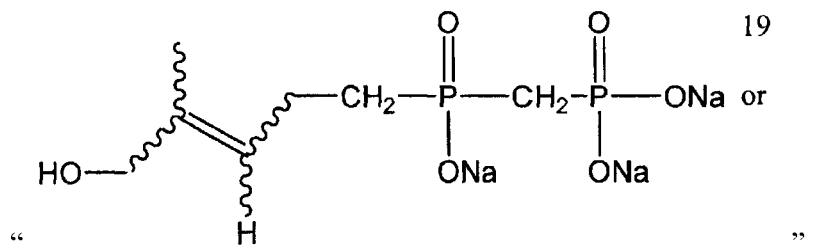

"

should read

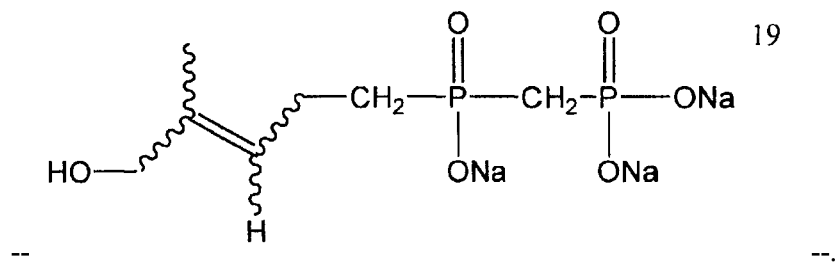

--.

Column 20,
Line 15,

"

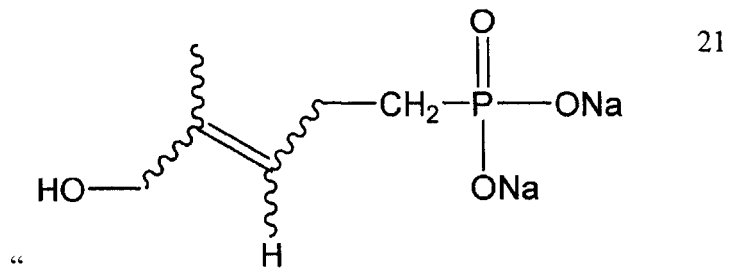

"

should read

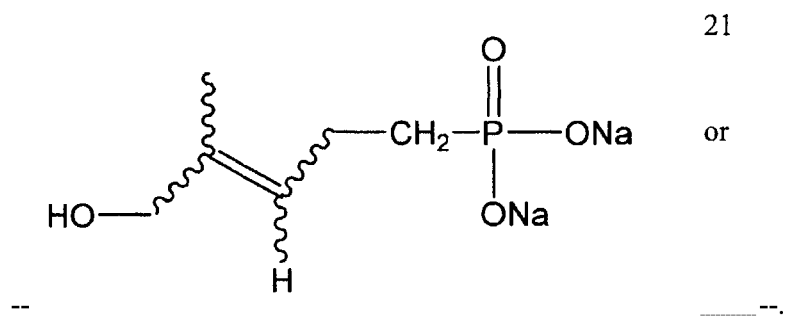

--.

UNITED STATES PATENT AND TRADEMARK OFFICE
CERTIFICATE OF CORRECTION

| | |
|---|---|
| PATENT NO. | : 7,871,992 B2 |
| APPLICATION NO. | : 12/137241 |
| DATED | : January 18, 2011 |
| INVENTOR(S) | : Hassan Jomaa et al. |

It is certified that error appears in the above-identified patent and that said Letters Patent is hereby corrected as shown below:

Column 6,
Lines 55-60,

" 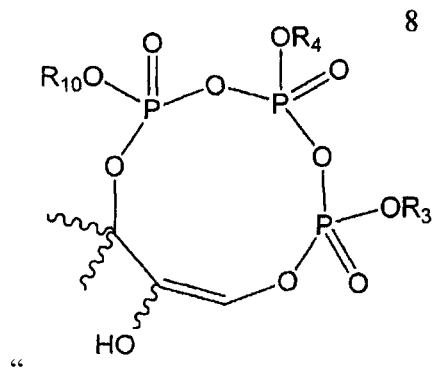 " should read -- 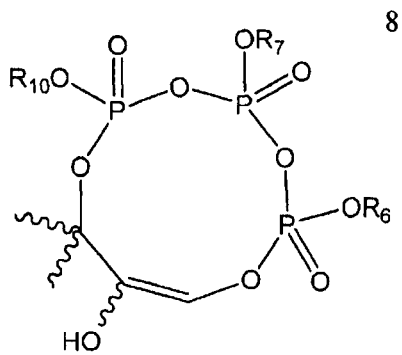 --.

Signed and Sealed this
Twenty-fourth Day of May, 2011

David J. Kappos
*Director of the United States Patent and Trademark Office*